(12) United States Patent
Gnanapragasam

(10) Patent No.: US 11,478,230 B2
(45) Date of Patent: Oct. 25, 2022

(54) PROSTATE BIOPSY APPARATUS

(71) Applicants: Cambridge University Hospitals NHS Foundation Trust, Cambridge (GB); Cambridge Enterprise Limited, Cambridge (GB)

(72) Inventor: Vincent Gnanapragasam, Cambridge (GB)

(73) Assignee: CAMBRIDGE UNIVERSITY HOSPITALS NHS FOUNDATION TRUST, Cambridge (GB)

( * ) Notice: Subject to any disclaimer, the term of this patent is extended or adjusted under 35 U.S.C. 154(b) by 0 days.

(21) Appl. No.: 15/326,942

(22) PCT Filed: Jul. 16, 2015

(86) PCT No.: PCT/GB2015/052065
§ 371 (c)(1),
(2) Date: Jan. 17, 2017

(87) PCT Pub. No.: WO2016/009218
PCT Pub. Date: Jan. 21, 2016

(65) Prior Publication Data
US 2017/0196543 A1 Jul. 13, 2017

(30) Foreign Application Priority Data
Jul. 17, 2014 (GB) ..................... 1412726

(51) Int. Cl.
*A61B 10/02* (2006.01)
*A61B 17/34* (2006.01)
*A61B 90/00* (2016.01)

(52) U.S. Cl.
CPC ...... *A61B 10/0241* (2013.01); *A61B 10/0283* (2013.01); *A61B 17/3403* (2013.01);
(Continued)

(58) Field of Classification Search
CPC . A61B 10/0241; A61B 10/0233; A61B 10/02; A61B 10/0283; A61B 17/3403;
(Continued)

(56) References Cited

U.S. PATENT DOCUMENTS 4,230,123 A 10/1980 Hawkins, Jr.
5,257,632 A 11/1993 Turkel et al.
(Continued)

FOREIGN PATENT DOCUMENTS

CH 1731103 A1 * 12/2006 .......... A61B 10/025
EP 0153047 8/1985
(Continued)

OTHER PUBLICATIONS

European Search Report for corresponding Application No. 15753415.7, dated Sep. 29, 2020.
(Continued)

*Primary Examiner* — Tse W Chen
*Assistant Examiner* — Avery M Foley

(57) ABSTRACT

A perineal prostate biopsy apparatus comprising a cannula for reaching a prostate gland of an adult human male through his perineum; and a coaxial needle comprising a hollow needle shaft having an open piercing tip at its distal end and being arranged to lie within the cannula so that the piercing tip protrudes from a distal end of the cannula; and, a stylet adapted to lie within the hollow needle shaft so that a distal tip of the stylet closes the piercing tip of the needle.

20 Claims, 4 Drawing Sheets

(52) U.S. Cl.
CPC .............. *A61B 2017/3407* (2013.01); *A61B 2017/3413* (2013.01); *A61B 2017/3492* (2013.01); *A61B 2090/034* (2016.02); *A61B 2090/036* (2016.02)

(58) Field of Classification Search
CPC .............. A61B 10/3403; A61B 10/025; A61B 10/0266; A61B 10/0275; A61B 17/3423; A61B 17/3421; A61B 17/3447; A61B 2010/045; A61B 2017/3409; A61B 2017/3447; A61B 2017/3452; A61B 2017/3407; A61B 2017/3413; A61B 2017/3492; A61B 2090/033; A61B 2090/034; A61B 2090/036
See application file for complete search history.

(56) References Cited

U.S. PATENT DOCUMENTS

| | | | |
|---|---|---|---|
| 5,499,989 A | 3/1996 | LaBash | |
| 2002/0010502 A1* | 1/2002 | Trachtenberg | A61F 7/123 |
| | | | 607/102 |
| 2002/0061300 A1* | 5/2002 | Gokcen | A61P 13/08 |
| | | | 424/94.2 |
| 2006/0047253 A1* | 3/2006 | Hayman | A61B 17/34 |
| | | | 604/272 |
| 2008/0216239 A1* | 9/2008 | Luginbuhl | A61B 5/055 |
| | | | 5/601 |
| 2013/0046200 A1 | 2/2013 | Stauber | |
| 2017/0020623 A1* | 1/2017 | Glossop | A61B 34/10 |
| 2017/0105709 A1* | 4/2017 | Ellis | A61M 25/0102 |

FOREIGN PATENT DOCUMENTS

| | | |
|---|---|---|
| EP | 1731103 | 12/2006 |
| ES | 1094730 | 12/2013 |
| WO | 2010085841 | 5/2010 |

OTHER PUBLICATIONS

International Search Report and Written Opinion for PCT/GB2015/052065 dated Sep. 11, 2015.
Search Report for GB1412726.0 dated Jan. 22, 2015.

* cited by examiner

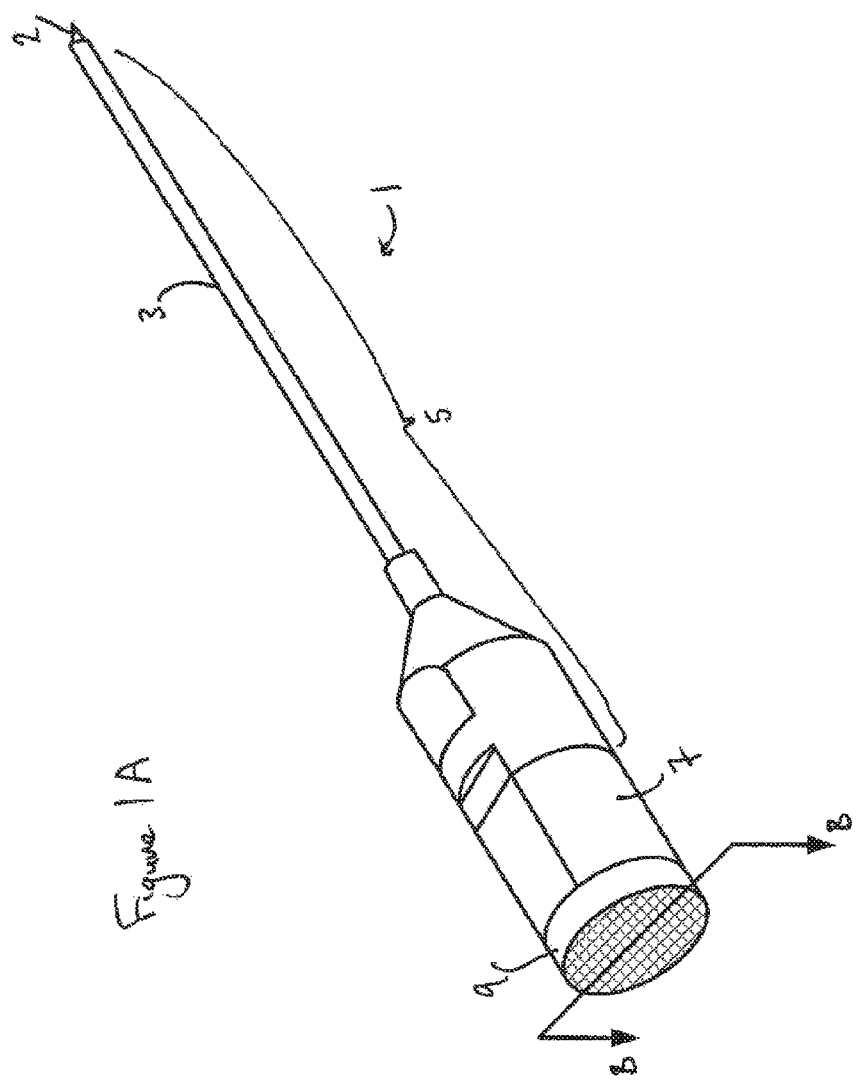

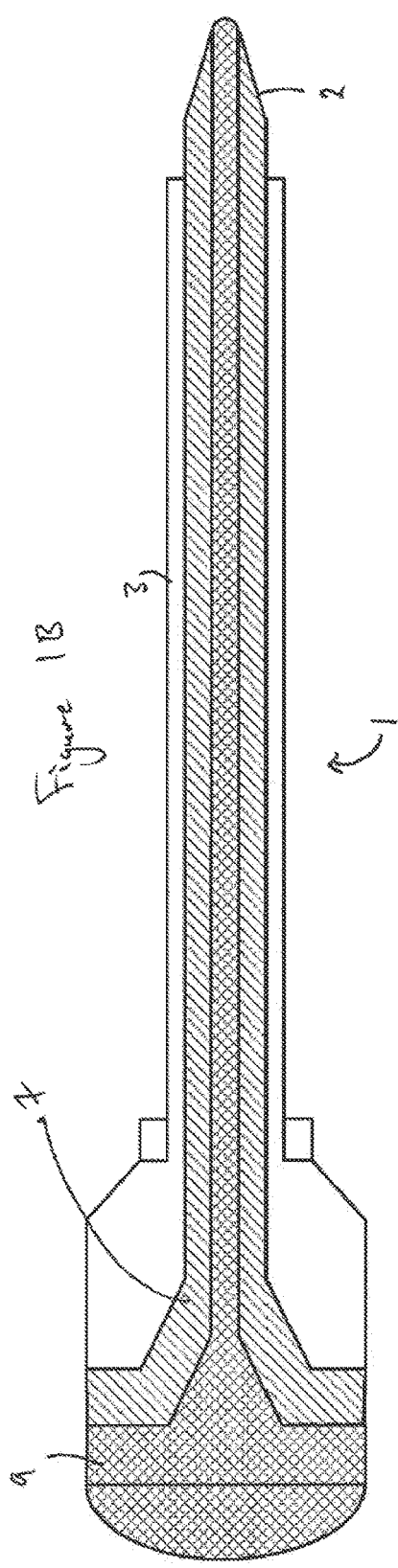
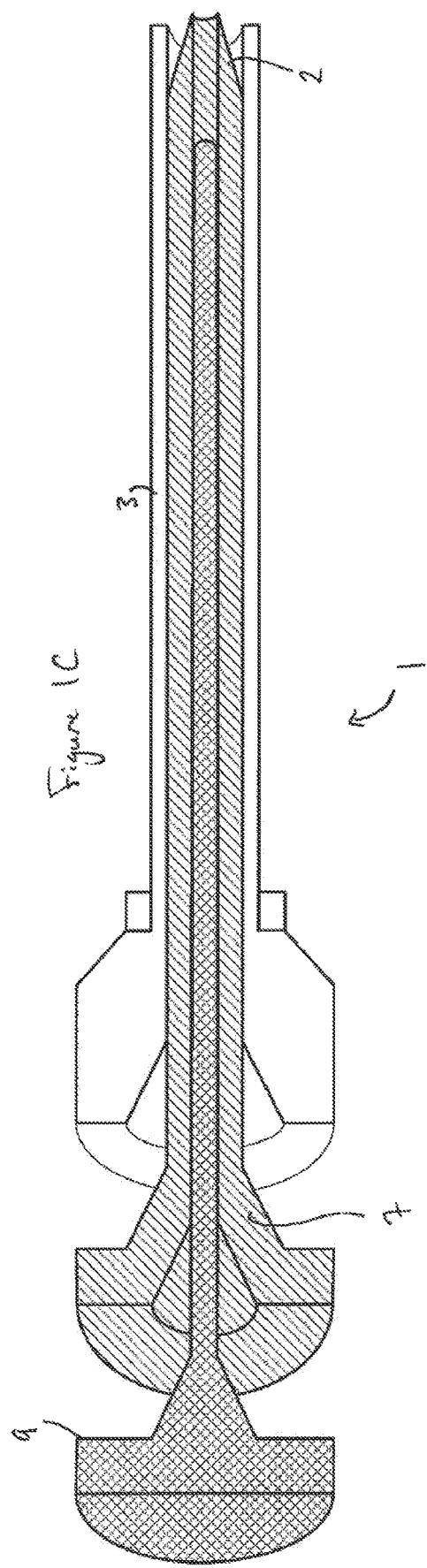

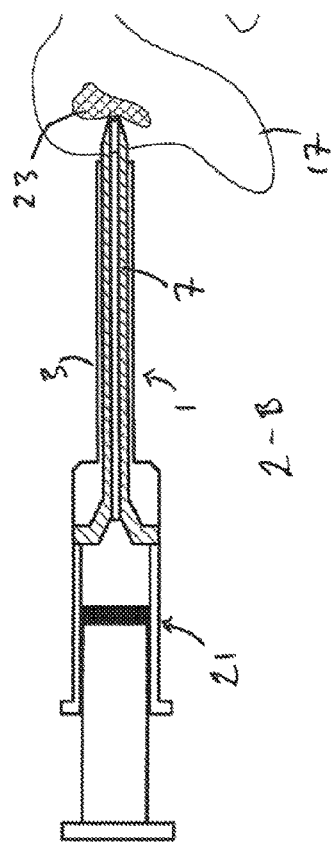
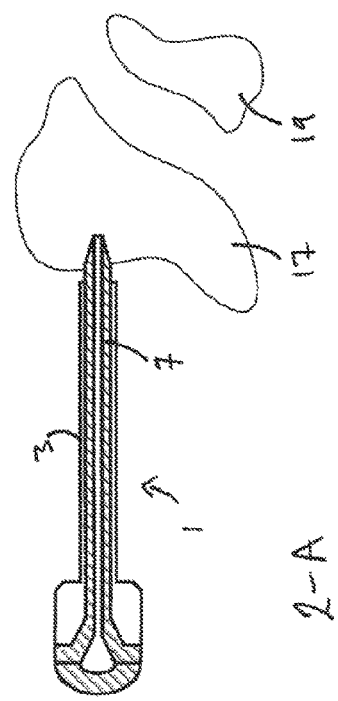
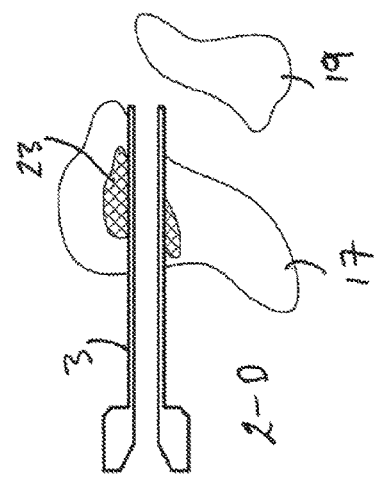
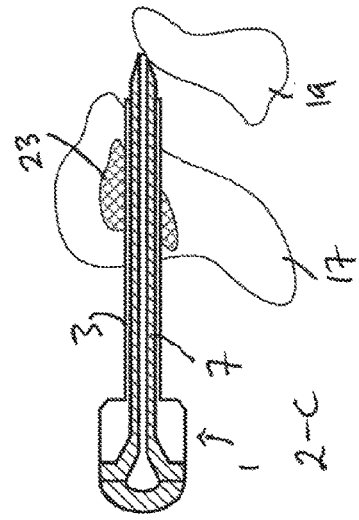
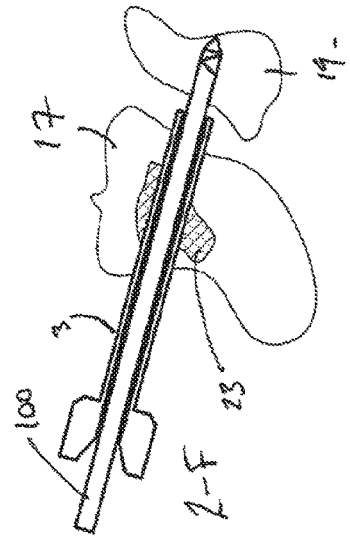
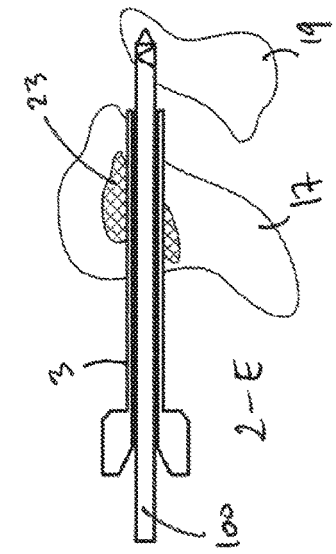
Figure 2

PROSTATE BIOPSY APPARATUS

The present invention relates to methods and apparatus for performing perineal biopsy of the prostate gland.

Prostate cancer is the most prevalent male cancer in the UK and its incidence is rising. The current method of diagnosing prostate cancer is with a needle biopsy of the prostate guided by a transrectal ultrasound probe inserted into the rectum. This method however carries a significant risk of bleeding (65%), fever (17%) and severe infections (1-2%) as the needle has to traverse the rectal wall a number of times. Moreover, 30% of cancers can be missed using this approach.

A safer and more accurate alternative is to biopsy the prostate through the perineum (perineal biopsies). This approach results in fewer infections and is more accurate in diagnosing prostate cancer. This method however requires multiple punctures of the perineum (between 24 and 40) and patients require a general anaesthetic.

Aspects of the present disclosure aim to enable a perineal biopsy to be undertaken in an outpatient clinic using local anaesthesia.

Some embodiments of the present disclosure will now be described, by way of example only, with reference to the accompanying drawings, in which:

FIG. 1A shows an elevation view of a perineal prostate biopsy apparatus;

FIG. 1B shows a section through the perineal prostate biopsy apparatus illustrated in FIG. 1A;

FIG. 1C shows a partially exploded view of the section view illustrated in FIG. 1;

FIG. 2 shows a series of schematic section views of illustrating use of a perineal prostate biopsy apparatus.

In the drawings like reference numerals are used to indicate like elements.

Figure 3:
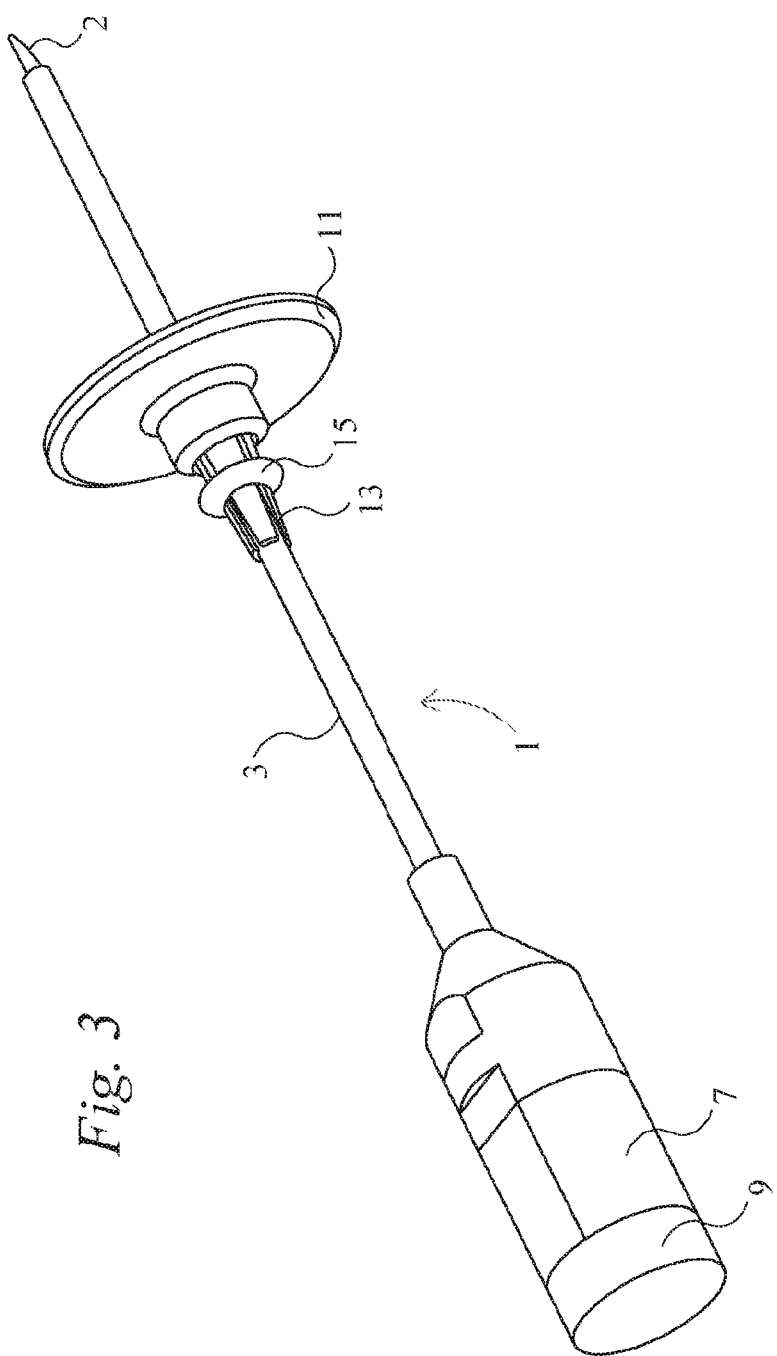
FIG. 3 shows an elevation view of a perineal prostate biopsy apparatus having a moveable flange.

Methods and apparatus of the present disclosure are suitable for accessing the prostate gland of an adult human male through the perineum to enable the collection of biopsy tissue samples.

Embodiments of the disclosure may provide access to the prostate in a minimally invasive manner, for example by gaining access to multiple sites distributed around the prostate gland via a single puncture site through the perineum.

Methods and apparatus of the disclosure enable a cannula to be inserted through a single puncture site where it can be left in position. A biopsy of the prostate can be obtained through this cannula, for example by using the cannula to guide a biopsy needle to a first site in the prostate gland. The orientation of the cannula can then be changed whilst it remains in position in the single puncture site. Another biopsy can then be obtained from a second site located in a different part of the prostate, e.g. spaced apart from the first site. This process of reorientation and sampling can be repeated to obtain multiple biopsies using a single puncture of the perineum.

The process may be performed under ultrasound guidance, for example provided by trans-rectal ultrasound probe. A single puncture site may be provided on each side of the perineum, and the same process performed from each puncture site. Accordingly, apparatus of the present disclosure may enable biopsies to be collected from across most areas, for example all areas, of the prostate from just two, or perhaps even only one, puncture site in the perineum.

Embodiments of the disclosure include a coaxial needle disposed inside a cannula. A blunt stylet may fill the channel within the coaxial needle. In embodiments of the disclosure this blunt stylet can be removed, for example before the coaxial needle is to be inserted into a patient. A syringe of local anaesthetic may then be attached to permit the coaxial needle to be inserted with concurrent infiltration of anaesthetic through the coaxial needle. For example, when the cannula has been partially (e.g. less than completely) inserted through the perineum anaesthetic can be injected through the coaxial needle to anaesthetise the puncture site in a manner which is highly localised to the site itself. The coaxial needle may comprise a proximal fluid coupling to allow local anaesthetic to be injected through the coaxial needle.

FIG. 1A shows a perineal prostate biopsy apparatus 1. FIG. 1B illustrates a section view of the plane indicated by the line B-B in FIG. 1A.

As illustrated in FIG. 1A, and FIG. 1B, the apparatus 1 comprises a cannula 5 sized for piercing a prostate gland of an adult human male through his perineum. The apparatus 1 also comprises a coaxial needle 7 having a piercing tip 2 at its distal end and a hollow needle shaft. The needle shaft is adapted to pass through the cannula 5 so that its piercing tip 2 can protrude from the distal end of the cannula 5.

The hollow needle shaft comprises an axial channel that is open at the piercing tip 2 of the needle. A blunt tipped stylet 9 may also be provided and adapted to lie within the hollow needle shaft so that the blunt tip of the stylet 9 closes the open piercing tip 2 of the hollow needle shaft.

The cannula 5 comprises a shaft 3 having a channel running through it to an opening at its distal end. The proximal end of the cannula 5 may comprise a handle body that is wider than the shaft, and may also comprise funnel shaped opening having a wide mouth disposed on the proximal face of the handle body. This funnel shaped opening is joined by the channel of the cannula 5 (which is narrower than the mouth) to the opening at the distal end of the cannula 5. The mouth of this funnel shaped opening may be at least 0.3 cm across, for example at least 0.5 cm, for example at least 0.6 cm, for example less than 10 cm, for example less than 5 cm, for example less than 2 cm. In one possibility the mouth of this funnel shaped opening may be about 0.7 cm across, for example it may be round and may have a diameter of about 0.7 cm. The funnel shaped opening may taper to an opening of the channel of less than 3 mm, for example less than 2 mm, for example about 1.3 mm.

The distal end of the cannula 5 is blunt, for example the tip of the cannula 5 may be "atraumatic", for example it may be smooth and may comprise only rounded edges having a sufficiently large radius of curvature so the edges can be moved along a surface of human tissue structure, such as tissue of the prostate gland, without puncturing, cutting, or tearing the tissue. If the position of the cannula needs to be changed, the coaxial needle can be re-inserted into the cannula to enable anaesthetic to be added as the cannula is moved if required.

The length of the cannula shaft 3 is selected to enable the cannula 5 to reach a number of different parts of the prostate gland of an adult human male by insertion through his perineum whilst the proximal handle remains outside his body. The length of the cannula shaft 3 may be at least 4 cm, for example at least 6 cm, for example between 7 and 9 cm, for example about 8 cm. The length of the shaft may be less than 20 cm, for example less than 15 cm. The outer diameter of the shaft may be at least 2 mm, for example about 2.2 mm, for example less than 5 mm, for example less than 3 mm.

The inner diameter of the shaft may be less than 2 mm, for example less than 1.5 mm, for example about 1.3 mm, for example at least 1 mm.

The outer diameter of the cannula shaft 3 is generally at least 2 mm, for example about 2.26 mm, for example less than 3 mm. The cannula shaft may comprise steel, such as surgical steel, and may be rigid.

The size of the opening at the distal end of the cannula 5 is selected to fit the piercing tip 2 of the coaxial needle 7 snugly so that the opening can be completely filled by the tip of the needle, for example the opening may be no more than 10% wider than the needle tip. The outer diameter of the cannula 5 may be low profile with respect to the width of the needle tip, for example no more than 10% wider than it. The piercing tip 2 of the needle can then pierce a sufficiently large hole through the perineum to enable the blunt cannula 5 to be inserted with it. The diameter of the piercing tip 2 of the needle 7 may be at least 0.7 mm, for example less than 0.9 mm, for example about 0.8 mm. The diameter of the coaxial needle 7 may be selected based on the diameter of a biopsy needle used to obtain samples once the cannula position is correct. The biopsy needle may be an 18 G (approx. 1.27 mm) needle, but other sizes of biopsy needle may also be used.

As noted above, the coaxial needle 7 comprises a hollow shaft. This shaft has a channel running through it from a fluid coupling at its proximal end to an open piercing tip 2 at its distal end. The fluid coupling may be adapted to enable the injection of fluids such as local anaesthetic through the needle.

As illustrated in FIG. 1A and FIG. 1B, the coaxial needle 7 comprises a proximal body that is wider than the needle's shaft. The distal side of this body provides a shoulder that is adapted to abut the handle body of the cannula 5. This shoulder may be arranged so that driving the needle distally into tissue also carries the cannula shaft 3 into the tissue. The needle's shoulder may be configured to be sufficiently robust to drive the cannula shaft 3 through the perineum.

The needle shaft extends distally from this shoulder to a distal piercing tip 2. The length of the needle shaft is selected so that, when the needle is within the cannula 5 and the needle shoulder abuts the cannula handle, the piercing tip 2 protrudes from the distal end of the cannula 5 and the needle shaft is supported by the cannula shaft 3. In this configuration the cannula 5 may reinforce and support the needle shaft to assist in puncturing the perineum. For example, the cannula shaft 3 may extend along most of the length, for example nearly the entire length of the needle's shaft (e.g. 90% or 95% or more of the length). In this configuration only the sharpened piercing tip 2 may protrude from the cannula 5 when the shoulder of the needle abuts the proximal handle body of the cannula 5. The cannula and the needle are both rigid and act to reinforce each other. This enables the cannula and needle to be driven together into the perineum.

As illustrated in FIG. 1B the stylet 9 is configured to fill the channel inside the hollow body of the coaxial needle 7. The tip of the stylet 9 may be blunt. In the arrangement illustrated in FIG. 1B and FIG. 1C it can be seen that, as with the needle, the stylet 9 may comprise a proximal body that is wider than the shaft of the stylet 9. This body of the stylet 9 has a shoulder adapted to be seated against the proximal side of the end of the hollow needle shaft. The stylet's shoulder thereby limits the distal advancement of the stylet 9 with respect to the cannula 5.

Embodiments of the disclosure may permit the cannula 5, and coaxial needle 7, to be deployed one-handed. When the coaxial needle 7 is fully inserted into the cannula the proximal bodies of the needle and cannula may cooperate to provide a single integrated handle for one handed manipulation of the apparatus. The needle 7 may be keyed, for example the shoulder of the needle may be at least partially non circular or otherwise asymmetric and arranged to mate with a complementarily shaped element of the shoulder of the cannula. This may inhibit rotation of the needle with respect to the cannula.

The stylet 9 is may be removed from within the needle before the device is used. For example, the blunt stylet tip may protrude from the piercing tip of the needle to protect the user. In some method embodiments the stylet may be reinserted into the needle when the device is in place in the perineum but being moved, reoriented, or removed. This may further inhibit trauma to perineal tissue.

The length of the stylet 9 from this shoulder may be chosen so that when the stylet 9 is within the needle and the stylet's shoulder abuts the needle's proximal shoulder, the blunt distal tip of the stylet 9 closes the open piercing tip 2 at the distal end of the hollow needle shaft.

As best seen in FIG. 1C, the stylet 9 may be removed from within the coaxial needle 7 by withdrawing it proximally. This need not displace the needle with respect to the cannula.

The proximal end of the coaxial needle 7 may comprise a fluid coupling for coupling the coaxial needle 7 to a supply of local anaesthetic such as a syringe. This may permit local anaesthetic to be administered through the coaxial needle 7.

Operation of this apparatus will now be described with reference to FIG. 2. FIG. 2 provides a series of schematic illustrations, 2-A to 2-F, of section views of use of the device of the present disclosure. Although not illustrated in FIG. 2, during the procedure described, a trans-rectal ultrasound probe may be used to guide positioning of the cannula. A clinician can manipulate the trans-rectal ultrasound probe with one hand whilst operating the perineal prostate biopsy apparatus 1 with the other.

When the apparatus is to be used, a small amount local anaesthetic may be infiltrated into the skin at or near the intended puncture site. A syringe or other supply of local anaesthetic may then be attached to the needle 7. The needle 7 and cannula may then be inserted under ultrasound guidance and with concurrent (e.g. continuous or intermittent) infiltration of local anaesthetic into the tissue of the puncture site through the needle 7 with the needle engaged into cannula shaft 3.

As shown in FIG. 2-A, the perineal prostate biopsy apparatus 1 may be pushed into the perineum 17 with the stylet 9 removed and the coaxial needle 7 fully inserted in the cannula shaft 3. By pushing on the proximal end of the needle 7, the piercing tip 2 of the needle can be advanced to carry the cannula 5 into the perineum.

When the cannula 5 has partially, for example less than completely, passed through the structures of the perineum 17*a* supply of local anaesthetic 21, for example a fluid provider such as a syringe or other fluid pump, may be used to administer local anaesthetic through the fluid coupling of the coaxial needle 7. Local anaesthetic can thereby be infiltrated to the tissue through the coaxial needle 7. Accordingly, embodiments of the disclosure enable administration of local anaesthetic to a highly localised region 23. Importantly this infiltration of local anaesthetic can be provided from within the puncture site and without withdrawing the cannula 5.

Once the local anaesthetic has taken effect, the cannula 5 can be further advanced into the tissue behind the piercing tip 2 of the needle. If necessary, additional local anaesthetic can be infiltrated into the tissue using the method described above at other sites deeper into the tissue as the cannula is advanced further into the perineum 17. As illustrated in FIG. 2-C, by following the approach, once the cannula has passed through the perineum 17, a considerable part 23, and perhaps all of, the tissue in contact with the cannula may have been anaesthetised. Embodiments of the disclosure enable this effect to be highly localised so that more anaesthetic is administered to the puncture site than to other regions of the perineum 17.

As illustrated in FIG. 2-D, the coaxial needle 7 can then be withdrawn leaving the cannula in position. As illustrated in FIG. 2-E, a biopsy needle 100 can then be deployed through the cannula and into the prostate gland 19 to obtain a biopsy from a first site in the prostate gland 19.

The biopsy needle can then be withdrawn, and the orientation of the cannula can be changed whilst the cannula remains in place in the anaesthetised puncture site in the perineum 17. As illustrated in FIG. 2-F, A biopsy needle 100 can then be deployed again with the cannula in this new orientation to obtain a second biopsy from a second site in the prostate gland 19. By repeating this process a series of biopsies can be obtained from a number of different regions of the prostate gland 19 through a single puncture of the perineum 17.

The first and second (and subsequent) sites may be spaced apart from each other in a medial-lateral direction, and/or in an anterior-posterior direction, and/or in an inferior superior direction. For example the two biopsies may be obtained from two distinct, separate, traverses and sampling of tissue of the prostate gland 19 by the biopsy needle.

FIG. 3 shows a perineal prostate biopsy apparatus 1 similar to that described above with reference to FIG. 1A and FIG. 1B. The apparatus 1 shown in FIG. 3 however further comprises a movable flange 11 which, in the example illustrated in FIG. 3, is provided by an annular disc. This extends radially out from the cannula body, and is adapted to be moved along the length of the cannula shaft to change the proximal-distal position of the flange 11 along the shaft. The flange 11 is adapted to be adhered to the perineum, so that it can hold the cannula in position. The flange 11 may also limit distal advancement of the apparatus 1 further into the perineum than may be desired.

As illustrated in FIG. 3, the flange 11 is carried on a grip mounting 13 which is operable to selectively grip or release the cannula shaft to enable the flange 11 to be either moved along the cannula shaft, or to be fixed in place upon it.

One example of a grip mounting 13 is illustrated in FIG. 3 and comprises at least two grippers adapted to lie adjacent a portion of the cannula shaft. The grippers are arranged so that, when urged radially inwards they grip the cannula shaft to hold the flange 11 in position.

The grippers may be tapered in a proximal-distal direction, and may comprise a groove or ridge around them to receive a resilient band 15. The resilient band 15 may be slid over the narrow tapered end of the grippers, and pushed in a proximal-distal direction over the grippers to stretch the band 15, until the band 15 slips into the groove (or over the ridge) to hold the band 15 in place whilst it urges the grippers against the cannula shaft to hold the flange 11 in place.

It will be appreciated in the context of the present disclosure that this flange 11 need not be disc shaped, for example a bar or rectangular plate may be used. Embodiments of this grip mounting 13 may permit one handed operation of the grip mounting 13 and flange 11. It will also be appreciated that other gripping mechanisms may be used to selectively hold the grip mounting 13 in place, for example a collar or clamp, for example a hose-clip, for example a ratcheted band such as a cable-tie.

Embodiments of the disclosure provide kits comprising at least one flange, at least one grip mounting and at least one perineal prostate biopsy apparatus as described herein. These kits may be sealed in a sterile pack for distribution and storage.

To the extent that certain methods may be applied to the living human or animal body, it will be appreciated that such methods may not provide any surgical or therapeutic effect, for example they may be applied ex vivo, for example to samples that are not part of the living human or animal body. For example, the methods described herein may be practiced on joints of meat, animal carcasses, human cadavers, and other non-living objects. For example tissue samples may be collected from the prostate glands of the cadavers of adult human males using the methods and apparatus described herein.

With reference to the drawings in general, it will be appreciated that schematic functional block diagrams are used to indicate functionality of systems and apparatus described herein. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A perineal prostate biopsy apparatus comprising:
 a cannula for reaching a prostate gland of an adult human male through his perineum, the cannula having a hollow cannula shaft;
 a coaxial needle comprising a hollow needle shaft having an open piercing tip at its distal end and being arranged to lie within the cannula shaft so that the piercing tip protrudes from a distal end of the cannula; and
 a movable flange that extends radially out from a body of the cannula;
 wherein the cannula and coaxial needle each comprise a proximal body adapted so that, when the coaxial needle is inserted into the cannula shaft, the proximal body of the cannula and the proximal body of the coaxial needle cooperate to provide a single integrated handle suitable for one-handed manipulation of the apparatus;
 wherein the proximal body of the coaxial needle has a shoulder which is arranged to abut the proximal body of the cannula, wherein the cannula and the coaxial needle are both sufficiently rigid and robust so that when the coaxial needle is inserted into the cannula shaft, the shoulder of the coaxial needle abuts the proximal body of the cannula and the two act to reinforce one another to enable the cannula and the needle to be driven together into the perineum with: (i) the piercing tip of the coaxial needle piercing a hole at a puncture site in the perineum and advancing distally therein, and (ii) the shoulder of the coaxial needle engaging the proximal body of the cannula to drive the cannula through the hole at the puncture site in the perineum and distally into the perineum as the coaxial needle advances distally into the perineum;

wherein the flange is carried on a grip mounting, wherein the grip mounting is arranged to move the flange along the cannula and to selectively grip the cannula to hold the flange fixed in place upon the cannula at a desired location on the cannula;

wherein the flange is adapted to adhere to the perineum to hold the cannula in position to enable:

(i) a biopsy to be obtained through the cannula shaft from a first site within the prostate gland, with the grip mounting gripping the cannula to hold the flange fixed in place upon the cannula and with the flange adhered to the perineum to hold the cannula fixed in position at the puncture site;

(ii) an orientation of the cannula to be changed whilst the cannula remains inserted in the puncture site in the perineum; and (iii) a biopsy to be obtained through the cannula shaft from a second site within the prostate gland, with the grip mounting gripping the cannula to hold the flange fixed in place upon the cannula and with the flange adhered to the perineum to hold the cannula fixed in position at the puncture site, wherein the second site is spaced apart from the first site.

2. The apparatus of claim 1 wherein a proximal end of the proximal body of the cannula comprises a funnel shaped guide for guiding the coaxial needle into the cannula.

3. The apparatus of claim 1 further comprising a stylet, wherein the stylet comprises a proximal shoulder adapted to be seated against the needle arranged so that when the stylet is within the coaxial needle and the proximal shoulder of the stylet abuts the coaxial needle a distal tip of the stylet is positioned in the open piercing tip of the coaxial needle.

4. The apparatus of claim 1 further comprising a stylet, wherein the stylet is adapted to be removed from the coaxial needle to allow injection of local anaesthetic through the coaxial needle during insertion of the cannula through the perineum.

5. The apparatus of claim 1 comprising a stylet adapted to lie within the hollow needle shaft so that a distal tip of the stylet closes the piercing tip of the coaxial needle.

6. A kit comprising the apparatus of claim 1 in a sealed sterile packet.

7. The apparatus of claim 1, wherein a size of the opening at the distal end of the cannula is selected to fit the piercing tip of the coaxial needle snugly so that the opening at the distal end of the cannula is filled by the piercing tip of the coaxial needle when the coaxial needle is inserted into the channel of the cannula.

8. The apparatus of claim 7, wherein the opening at the distal end of the cannula is no more than 10% wider than the piercing tip of the coaxial needle.

9. The apparatus of claim 1, wherein the needle shaft has a fluid coupling port at its proximal end, and wherein the needle shaft is hollow to define an axial channel extending from the fluid coupling port at the proximal end of the needle shaft to the open piercing tip at the distal end of the needle shaft to enable anaesthetic to be injected through the fluid coupling port and delivered to the perineum; and wherein the axial channel of the coaxial needle is arranged to enable anaesthetic to be injected through the fluid coupling port and into the perineum during insertion of the coaxial needle and cannula into the perineum so that once the cannula has passed through the perineum, a majority of the tissue in contact with the cannula has been anaesthetised.

10. The apparatus of claim 1, wherein the coaxial needle and the cannula are arranged to enable the coaxial needle to be guided to a first site in the prostate gland by controlling movement of the cannula.

11. The apparatus of claim 1, wherein a distal end of the cannula is blunt and atraumatic to enable the cannula to be moved along tissue of the prostate gland without the distal end of the cannula puncturing, cutting, and/or tearing the tissue of the prostate gland.

12. The apparatus of claim 11, wherein the cannula extends along a majority of the length of the hollow needle shaft of the coaxial needle so that, when the shoulder of the coaxial needle abuts the proximal body of the cannula, only the piercing tip of the coaxial needle protrudes out of the distal end of the cannula.

13. The apparatus of claim 12, wherein the coaxial needle and the cannula are arranged to inhibit rotation of the coaxial needle relative to the cannula when the coaxial needle is inserted into the cannula shaft so that the piercing tip of the coaxial needle remains in a fixed rotational orientation relative to the cannula.

14. The apparatus of claim 13, wherein the cannula has a length of between 4 cm and 20 cm.

15. The apparatus of claim 14, wherein the cannula has a hollow cannula shaft having an outer diameter of between 2 mm and 5 mm and an inner diameter of between 1 mm and 2 mm.

16. The apparatus of claim 15, wherein the piercing tip of the coaxial needle has a diameter of between 0.7 mm and 0.9 mm.

17. The apparatus of claim 16, wherein the flange is adapted to adhere to the perineum to hold the cannula in position to enable the coaxial needle to be withdrawn, with the grip mounting gripping the cannula to hold the flange fixed in place upon the cannula and with the flange adhered to the perineum to hold the cannula fixed in position at the puncture site.

18. A method comprising:

inserting a cannula and a coaxial needle together into a puncture site in a perineum of a human male, wherein the coaxial needle comprises: (i) a hollow needle shaft having an open piercing tip at its distal end and a fluid coupling at its proximal end to enable anaesthetic to be injected through the needle to the perineum during insertion of the coaxial needle and cannula into the perineum, and (ii) a shoulder located at its proximal end, and wherein the cannula comprises a proximal body located at its proximal end, and wherein the coaxial needle is arranged to lie within the cannula so that the piercing tip protrudes from a distal end of the cannula and the shoulder of the coaxial needle abuts the proximal body of the cannula, and wherein inserting the cannula and coaxial needle together into the perineum comprises: (a) driving the coaxial needle into the perineum to pierce a hole in the perineum and advance distally therein with the shoulder of the coaxial needle engaging the proximal body of the cannula to drive the cannula through the hole and distally into the perineum as the coaxial needle advances distally into the perineum, and (b) controlling movement of the cannula to guide the coaxial needle to a first site in a prostate gland of the human male;

adhering a movable flange which extends radially out from a body of the cannula to the perineum, wherein the flange is carried on a grip mounting arranged to selectively grip the cannula to hold the flange fixed in place upon the cannula at a desired location on the cannula, using the grip mounting to selectively grip the movable flange to the cannula to hold the flange fixed in place upon the cannula with the flange adhered to the perineum to hold the cannula fixed in position at the puncture site, obtaining, through the cannula, a first biopsy from the first site in the prostate gland of the human male;

changing an orientation of the cannula with respect to the perineum whilst the cannula remains in the puncture site and adhered to the perineum via the movable flange; and, obtaining, through the cannula, a second biopsy from a second site in the prostate gland, with the grip mounting gripping the cannula to hold the flange fixed in place upon the cannula with the flange adhered to the perineum to hold the cannula fixed in position at the puncture site, wherein the second site is spaced apart from the first site; and wherein inserting the cannula comprises advancing the cannula partially into the perineum, opening a channel through the cannula, and delivering local anaesthetic through the channel into the perineum, and advancing the cannula further into the perineum towards the first site in the prostate gland so that once the cannula has passed through the perineum, a majority of the tissue in contact with the cannula has been anaesthetised.

19. The method of claim 18 wherein the channel comprises a channel of the coaxial needle.

20. A perineal prostate biopsy apparatus comprising:

a channel means for providing access to a prostate gland of an adult human male through his perineum; and a piercing means for piercing the perineum, wherein the piercing means comprises a shaft having fluid coupling means at its proximal end and an open piercing tip at its distal end;

wherein the piercing means is arranged to lie within the channel means so that the piercing tip of the piercing means protrudes from a distal end of the channel means;

wherein the piercing means is hollow to define an axial channel extending from the fluid coupling means at the proximal end of the shaft to the open piercing tip at the distal end of the shaft to enable anaesthetic to be injected through the fluid coupling means and delivered to the perineum;

wherein the channel means comprises a proximal body located at its proximal end, and the piercing means comprises a shoulder located at its proximal end, wherein the shoulder of the piercing means is arranged to abut the proximal body of the channel means;

wherein the channel means and the piercing means are both sufficiently rigid and robust so that when the piercing means is inserted into a shaft of the channel means, the shoulder of the piercing means abuts the proximal body of the channel means and the two act to reinforce one another to enable the channel means and the piercing means to be driven together into the perineum with: (i) the piercing means piercing a hole in the perineum and advancing distally therein, and (ii) the shoulder of the piercing means engaging the proximal body of the channel means to drive the channel means through the hole and distally into the perineum as the piercing means advances distally into the perineum;

wherein the proximal body of the channel means and the shoulder of the piercing means cooperate to provide a single integrated handle suitable for one-handed insertion of the channel means and piercing means together into the perineum, and wherein the piercing means and the channel means are arranged to enable the piercing means to be guided to a first site in the prostate gland by controlling movement of the channel means, wherein the axial channel of the piercing means is arranged to enable anaesthetic to be injected through the fluid coupling means and into the perineum during insertion of the piercing means and the channel means into the perineum so that once the channel means has passed through the perineum, a majority of the tissue in contact with the channel means has been anaesthetized, wherein the perineal prostate biopsy apparatus further comprises a movable flange extending radially out from the channel means, and wherein the flange is carried on a grip mounting, wherein the grip mounting is arranged to move the flange along the channel means and to selectively grip the channel means to hold the flange fixed in place upon the channel means at a desired location on the channel means, and wherein the movable flange is adapted to adhere to the perineum to hold the channel means in position to enable:

(i) a biopsy to be obtained through the channel means from a first site within the prostate gland, with the grip mounting gripping the channel means to hold the flange fixed in place upon the channel means and with the flange adhered to the perineum to hold the channel means fixed in position at the puncture site;

(ii) an orientation of the channel means to be changed whilst the channel means remains inserted in the puncture site in the perineum; and (iii) a biopsy to be obtained through the channel means from a second site within the prostate gland, with the grip mounting gripping the channel means to hold the flange fixed in place upon the channel means and with the flange adhered to the perineum to hold the channel means fixed in position at the puncture site, wherein the second site is spaced apart from the first site.

* * * * *